United States Patent [19]

Tsuneki et al.

[11] Patent Number: 5,663,480
[45] Date of Patent: Sep. 2, 1997

[54] SYNTHESIS OF AROMATIC CARBONATES BY TRANSESTERIFICATION USING A CATALYST COMPRISING A MICROPOROUS MATERIAL AND A GROUP IV METAL

[75] Inventors: Hideaki Tsuneki, Tokyo; Masaru Kirishiki; Kenichi Watanabe, both of Osaka; Yoshiyuki Onda, Tokyo, all of Japan

[73] Assignee: Nippon Shokubai Co., Ltd., Osaka, Japan

[21] Appl. No.: 680,223

[22] Filed: Jul. 11, 1996

Related U.S. Application Data

[62] Division of Ser. No. 397,117, Dec. 16, 1994, Pat. No. 5,565,605.

[30] Foreign Application Priority Data

Dec. 20, 1993 [JP] Japan ................... 5-319872
Sep. 21, 1994 [JP] Japan ................... 6-226172

[51] Int. Cl.$^6$ ................... C07C 68/06
[52] U.S. Cl. ................... 558/270; 558/271; 558/274
[58] Field of Search ................... 558/270, 271, 558/274

[56] References Cited

U.S. PATENT DOCUMENTS

| 3,328,439 | 6/1967 | Hamilton ................... 560/109 X |
| 4,182,726 | 1/1980 | Illuminati et al. ................... 260/463 |
| 4,721,609 | 1/1988 | Baacke et al. ................... 423/329 |
| 5,049,366 | 9/1991 | Clark et al. ................... 423/277 |
| 5,082,641 | 1/1992 | Popa et al. ................... 423/326 |
| 5,166,393 | 11/1992 | Fukuoka et al. ................... 558/274 |
| 5,210,268 | 5/1993 | Fukuoka et al. ................... 558/270 |
| 5,244,650 | 9/1993 | Kuznicki et al. ................... 423/718 |
| 5,354,923 | 10/1994 | Schon et al. ................... 558/270 |

FOREIGN PATENT DOCUMENTS

| 0623581 | 11/1994 | European Pat. Off. . |
| 5271433 | 12/1975 | Japan . |
| 54-125617 | 9/1979 | Japan . |
| 61-5467 | 2/1986 | Japan . |
| 61-501981 | 9/1986 | Japan . |
| 61-200943 | 9/1986 | Japan . |
| 64-65013 | 3/1989 | Japan . |
| 2243506 | 9/1990 | Japan . |
| 3115249 | 5/1991 | Japan . |
| 49358 | 1/1992 | Japan . |
| 4266856 | 9/1992 | Japan . |
| 5503499 | 6/1993 | Japan . |
| 9111390 | 9/1979 | WIPO . |
| 8504853 | 11/1985 | WIPO . |

OTHER PUBLICATIONS

"The Preparation of Alkyltrimethylammonium–Kanemite Complexes and Their Conversion to Microporous Materials", Bull. Chem. Soc. Jpn., 63, 988–992 (1990).

"A New Family of Mesoporous Molecular Sieves Prepared with Liquid Crystal Templates", Beck et al., J. Am. Chem. Soc., 1992, 114, 10834–10843.

Lecture Preprint I, 67th Annual Spring Convention of Chemical Society of Japan, p. 484, Col. 3 L6 17, Mar. 14, 1994.

"Titanium–Containing Mesoporous Molecular Sieves for Catalytic Oxidation of Aromatic Compounds", Taneu et al., Letters to Nature, vol. 368, pp. 321–323, Mar. 24, 1994.

"Shape Selective Epoxidation of Alkenes Catalyzed by Titanosilicate", Tatsumi et al., Chem. Soc. Jpn., Chemistry Letters, pp. 297, 298 (1990).

"Structure of the Microporous Titanosilicate ETS–10", Anderson et al., Letters to Nature, vol. 367, pp. 347–351, Jan. 27, 1994.

"Handbook of Molecular Sieves", Szostak, pp. 470–471, 1992.

"Ullmann's Encyclopedia of Industrial Chemistry", 5th Ed., vol. 19A, (1985), pp. 300–301.

*Primary Examiner*—Johann Richter
*Assistant Examiner*—Michael G. Ambrose
*Attorney, Agent, or Firm*—Roylance, Abrams, Berdo & Goodman, L.L.P.

[57] ABSTRACT

A catalyst for producing an aryl ester of a carbonic or carboxylic acid is disclosed, which includes a microporous material containing a metal element belonging to group IV. This catalyst can be used as a heterogeneous catalyst to produce the aryl ester in high yield with industrial advantages. In order to produce the aryl ester using the catalyst, a carbonate or an aliphatic carboxylate is transesterified with an aromatic hydroxy compound, or an aryl carboxylate is transesterified with a carbonate, or an alkyl aryl carbonate is disproportionated by transesterification.

9 Claims, 2 Drawing Sheets

SYNTHESIS OF AROMATIC CARBONATES BY TRANSESTERIFICATION USING A CATALYST COMPRISING A MICROPOROUS MATERIAL AND A GROUP IV METAL

This application is a division of application Ser. No. 08/357,117, filed Dec. 16, 1994, now U.S. Pat. No. 5,565,605.

TECHNICAL FIELD

The present invention relates to a catalyst for producing aryl esters, such as aryl carbonates and aryl carboxylates, and also relates to a process for producing aryl esters using the catalyst.

BACKGROUND ART

As to processes for producing aryl carbonates, there are known, for example, the following processes: a process including a transesterification reaction between a carbonic acid ester and an aromatic hydroxy compound; and a process including disproportionation by a transesterification reaction of alkyl aryl carbonates. These transesterification reactions need catalysts. For the catalysts, there have been proposed various catalysts: for example, Lewis acids or compounds which produce Lewis acids; Ti-based or Al-based compounds; lead compounds; organotin compounds; and so forth.

In addition, as to processes for producing aryl carboxylates, there are known, for example, the following processes: a process including esterification of an aromatic hydroxy compound with an aliphatic carboxylic acid; a process including esterification of phenol with high active reaction materials, such as isopropenyl acetate and diketene; and so forth. However, any process using a solid heterogeneous catalyst is not yet known in industrial production processes including a transesterification reaction of an aliphatic carboxylate with an aromatic hydroxy compound.

All the catalysts used in the above-mentioned processes are homogeneous and react in condition of being dissolved in raw materials and so are difficult to separate after reactions. Therefore, these catalysts have problems in industrial practical use.

In order to solve the problems about separation, Japanese Official Patent Gazette (Kokoku) No. Showa 61-5467 proposed to use a silica-titania composite oxide as a heterogeneous catalyst, and Japanese Official Patent Provisional Publication (Kokai) No. Heisei 4-266856 proposed to use titanium oxide having high surface area as a catalyst. However, the silica-titania composite oxide catalyst has strong character as an acid and easily cause decarboxylation that is a side reaction; and the titanium oxide catalyst has low activity. In addition, although both the catalysts are heterogeneous at the initiation of a reaction, a considerably large proportion of catalyst components dissolve into raw materials as the reaction progresses. So these catalysts substantially do not differ from homogeneous ones at all, and are not sufficient as means of solving the problems.

DISCLOSURE OF THE INVENTION

OBJECTS OF THE INVENTION

It is an object of the present invention to provide a catalyst for producing an aryl ester in high yield and high selectivity with industrial advantages, the catalyst being easily separable after reaction.

It is another object of the present invention to provide a process for producing an aryl ester in high yield and high selectivity with industrial advantages, wherein there is used a catalyst that is insoluble in a reaction liquid, so the separation of the catalyst is easy after reaction.

SUMMARY OF THE INVENTION (1) A process for producing an aryl ester, according to a first aspect of the present invention, is a process for producing an aryl carbonate, which includes a step of carrying out transesterification between:

a carbonate shown by the following general formula (I):

$$(R^1O)CO(OR^2) \qquad (I)$$

where: $R^1$ denotes an alkyl group, a cycloalkyl group, an arylalkyl group, or an aryl group which may have a substituent; and $R^2$ denotes an alkyl group, a cycloalkyl group, or an arylalkyl group; and an aromatic hydroxy compound shown by the following general formula (II):

$$R^3OH \qquad (II)$$

where: $R^3$ denotes an aryl group which may have a substituent; in a liquid phase in the presence of a heterogeneous catalyst including a microporous material containing a metal element belonging to group IV;

whereby there is obtained an aryl carbonate shown by the following general formula (III):

$$(R^1O)CO(OR^3) \qquad (III)$$

where: $R^1$ denotes an alkyl group, a cycloalkyl group, an arylalkyl group, or an aryl group which may have a substituent; and $R^3$ denotes an aryl group which may have a substituent.

(2) A process for producing an aryl ester, according to a second aspect of the present invention, is a process for producing an aryl carboxylate, which includes a step of carrying out transesterification between:

an aliphatic carboxylate shown by the following general formula (IV):

$$R^2COOR^4 \qquad (IV)$$

where: $R^2$ denotes an alkyl group, a cycloalkyl group, or an arylalkyl group; and $R^4$ denotes an alkyl group, a cycloalkyl group, or an arylalkyl group; and an aromatic hydroxy compound shown by the following general formula (II):

$$R^3OH \qquad (II)$$

where: $R^3$ denotes an aryl group which may have a substituent; in a liquid phase in the presence of a heterogeneous catalyst including a microporous material containing a metal element belonging to group IV;

whereby there is obtained an aryl carboxylate shown by the following general formula (V):

$$R^2COOR^3 \qquad (V)$$

where: $R^2$ denotes an alkyl group, a cycloalkyl group, or an arylalkyl group; and $R^3$ denotes an aryl group which may have a substituent.

(3) A process for producing an aryl ester, according to a third aspect of the present invention, is a process for producing a diaryl carbonate, which includes a step of carrying out a disproportionation reaction by transesterification of an alkyl aryl carbonate shown by the following general formula (VI):

$$(R^2O)CO(OR^3) \quad (VI)$$

where: $R^2$ denotes an alkyl group, a cycloalkyl group, or an arylalkyl group; and $R^3$ denotes an aryl group which may have a substituent; in a liquid phase in the presence of a heterogeneous catalyst including a microporous material containing a metal element belonging to group IV;

whereby there is obtained a diaryl carbonate shown by the following general formula (VII):

$$(R^3O)CO(OR^3) \quad (VII)$$

where: $R^3$ denotes an aryl group which may have a substituent.

(4) A process for producing an aryl ester, according to a fourth aspect of the present invention, is a process for producing an aryl carbonate, which includes a step of carrying out transesterification between:

an aryl carboxylate shown by the following general formula (VIII):

$$R^5COOR^6 \quad (VIII)$$

where: $R^5$ denotes an alkyl group, a cycloalkyl group, or an arylalkyl group; and $R^6$ denotes an aryl group which may have a substituent; and a carbonate shown by the following general formula (I):

$$(R^1O)CO(OR^2) \quad (I)$$

where: $R^1$ denotes an alkyl group, a cycloalkyl group, an arylalkyl group, or an aryl group which may have a substituent; and $R^2$ denotes an alkyl group, a cycloalkyl group, or an arylalkyl group; in a liquid phase in the presence of a heterogeneous catalyst including a microporous material containing a metal element belonging to group IV;

whereby there is obtained an aryl carbonate shown by the following general formula (IX):

$$(R^7O)CO(OR^8) \quad (IX)$$

where: $R^7$ denotes an alkyl group, a cycloalkyl group, an arylalkyl group, or an aryl group which may have a substituent; and $R^8$ denotes an aryl group which may have a substituent.

(5) A catalyst of the present invention includes a microporous material containing a metal element belonging to group IV and is used in a process which includes a step of carrying out transesterification between:

a carbonate shown by the following general formula (I):

$$(R^1O)CO(OR^2) \quad (I)$$

where: $R^1$ denotes an alkyl group, a cycloalkyl group, an arylalkyl group, or an aryl group which may have a substituent; and $R^2$ denotes an alkyl group, a cycloalkyl group, or an arylalkyl group; and an aromatic hydroxy compound shown by the following general formula (II):

$$R^3OH \quad (II)$$

where: $R^3$ denotes an aryl group which may have a substituent; in a liquid phase in the presence of a catalyst;

whereby there is obtained an aryl carbonate shown by the following general formula (III):

$$(R^1O)CO(OR^3) \quad (III)$$

where: $R^1$ denotes an alkyl group, a cycloalkyl group, an arylalkyl group, or an aryl group which may have a substituent; and $R^3$ denotes an aryl group which may have a substituent.

(6) A catalyst of the present invention includes a microporous material containing a metal element belonging to group IV and is used in a process which includes a step of carrying out transesterification between:

an aliphatic carboxylate shown by the following general formula (IV):

$$R^2COOR^4 \quad (IV)$$

where: $R^2$ denotes an alkyl group, a cycloalkyl group, or an arylalkyl group; and $R^4$ denotes an alkyl group, a cycloalkyl group, or an arylalkyl group; and an aromatic hydroxy compound shown by the following general formula (II):

$$R^3OH \quad (II)$$

where: $R^3$ denotes an aryl group which may have a substituent; in a liquid phase in the presence of a catalyst;

whereby there is obtained an aryl carboxylate shown by the following general formula (V):

$$R^2COOR^3 \quad (V)$$

where: $R^2$ denotes an alkyl group, a cycloalkyl group, or an arylalkyl group; and $R^3$ denotes an aryl group which may have a substituent.

(7) A catalyst of the present invention includes a microporous material containing a metal element belonging to group IV and is used in a process which includes a step of carrying out a disproportionation reaction by transesterification of an alkyl aryl carbonate shown by the following general formula (VI):

$$(R^2O)CO(OR^3) \quad (VI)$$

where: $R^2$ denotes an alkyl group, a cycloalkyl group, or an arylalkyl group; and $R^3$ denotes an aryl group which may have a substituent; in a liquid phase in the presence of a catalyst;

whereby there is obtained a diaryl carbonate shown by the following general formula (VII):

$$(R^3O)CO(OR^3) \quad (VII)$$

where: $R^3$ denotes an aryl group which may have a substituent.

(8) A catalyst of the present invention includes a microporous material containing a metal element belonging to group IV and is used in a process which includes a step of carrying out transesterification between:

an aryl carboxylate shown by the following general formula (VIII):

$$R^5COOR^6 \quad (VIII)$$

where: $R^5$ denotes an alkyl group, a cycloalkyl group, or an arylalkyl group; and $R^6$ denotes an aryl group which may have a substituent; and a carbonate shown by the following general formula (I):

$$(R^1O)CO(OR^2) \quad (I)$$

where: $R^1$ denotes an alkyl group, a cycloalkyl group, an arylalkyl group, or an aryl group which may have a substituent; and $R^2$ denotes an alkyl group, a cycloalkyl group, or an arylalkyl group; in a liquid phase in the presence of a catalyst;

whereby there is obtained an aryl carbonate shown by the following general formula (IX):

where: $R^7$ denotes an alkyl group, a cycloalkyl group, an arylalkyl group, or an aryl group which may have a substituent; and $R^8$ denotes an aryl group which may have a substituent.

In the aforementioned processes (1) to (4), the microporous material containing a metal element belonging to group IV is preferred to be a metallosilicate or a metalloaluminophosphate.

In the aforementioned process (1) or (2), the microporous material containing a metal element belonging to group IV is more preferred to be a crystalline titanosilicate or a crystalline titanoaluminophosphate.

In the aforementioned process (3) or (4), the microporous material containing a metal element belonging to group IV is more preferred to be a mesoporous titanosilicate or a crystalline titanoaluminophosphate.

In the aforementioned catalysts (5) to (8), the microporous material containing a metal element belonging to group IV is preferred to be a metallosilicate or a metalloaluminophosphate.

In the aforementioned catalyst (5) or (6), the microporous material containing a metal element belonging to group IV is more preferred to be a crystalline titanosilicate or a crystalline titanoaluminophosphate.

In the aforementioned catalyst (7) or (8), the microporous material containing a metal element belonging to group IV is more preferred to be a mesoporous titanosilicate or a crystalline titanoaluminophosphate.

Hereinafter, the present invention is explained in detail.

The aryl esters relating to the present invention are, for example, aryl carbonates, diaryl carbonates, aryl carboxylates, and the like.

Production Process:

Of the aryl carbonates produced by the process (1), an alkyl aryl carbonate can be converted into a diaryl carbonate by carrying out a disproportionation reaction by transesterification in the presence of a heterogeneous catalyst including a microporous material containing a metal element belonging to group IV as in the process (3). This disproportionation reaction may be carried out in the presence of a known homogeneous catalyst containing titanium, tin, lead, or the like.

The aryl carboxylate produced by the process (2) can, for example, be converted into a aryl carbonate by carrying out its transesterification reaction with a carbonate in the presence of a heterogeneous catalyst including a microporous material containing a metal element belonging to group IV as in the process (4). This transesterification reaction may be carried out in the presence of a known homogeneous catalyst containing titanium, tin, lead, or the like.

The alkyl aryl carbonate, used in the process (3) that is an example of processes for producing the diaryl carbonate, can, for example, be obtained by carrying out, according to the process (1), a transesterification reaction of a carbonate with an aromatic hydroxy compound in the presence of a heterogeneous catalyst including a microporous material containing a metal element belonging to group IV. This transesterification reaction may be carried out in the presence of a known homogeneous catalyst containing titanium, tin, lead, or the like.

The aryl carboxylate, used in the process (4) that is an example of processes for producing the aryl carbonate, can, for example, be obtained by carrying out, according to the process (2), a transesterification reaction of an aliphatic carboxylate with an aromatic hydroxy compound in the presence of a heterogeneous catalyst including a microporous material containing a metal element belonging to group IV. This transesterification reaction may be carried out in the presence of a known homogeneous catalyst containing titanium, tin, lead, or the like.

The present invention does not include an embodiment wherein in the presence of a homogeneous catalyst, there are carried out both a post-stage reaction for producing an ultimately aimed aryl ester and a pre-stage reaction for producing an aryl ester that is used as a raw material for the post-stage reaction.

The carbonate, that is used as a raw material for a reaction carried out in the process (1), is not especially limited so long as it is that shown by the aforementioned general formula (I). However, its practical examples can be cited as follows: aliphatic carbonates, such as dimethyl carbonate, diethyl carbonate, n-propyl carbonate, isopropyl carbonate, dibutyl carbonate (including isomers), dipentyl carbonate (including isomers), dihexyl carbonate (including isomers), diheptyl carbonate (including isomers), dioctyl carbonate (including isomers), dinonyl carbonate (including isomers), didecyl carbonate (including isomers), dicyclohexyl carbonate (including isomers), dibenzyl carbonate (including isomers), diphenethyl carbonate (including isomers), and dimethylbenzyl carbonate (including isomers); alkyl aryl carbonates, such as methylphenyl carbonate and ethylphenyl carbonate. Any mixture of these compounds may also be used. Particularly, dimethyl carbonate is used as an industrially preferred example.

As to the aromatic hydroxy compound used as a raw material for a reaction carried out in the process (1) or (2), the following can be exemplified: phenol; o-, m-, or p-cresol; o-, m-, or p-chlorophenol; o-, m-, or p-ethylphenol; o-, m-, or p-isopropylphenol; o-, m-, or p-methoxyphenol; xylenols; α- or β-naphthol. Any mixture of these compounds may also be used. Particularly, phenol is used as an industrially preferred example.

The aliphatic carboxylate, that is used as a raw material for a reaction carried out in the process (2), is not especially limited so long as it is that shown by the aforementioned general formula (III). However, its practical examples can be cited as follows: methyl acetate, ethyl acetate, propyl acetate, butyl acetate, cyclohexyl acetate, benzyl acetate, 2-ethylhexyl acetate, methyl propionate, ethyl propionate, propyl propionate, butyl propionate, methyl butyrate, ethyl butyrate, propyl butyrate, methyl isobutyrate, ethyl isobutyrate, propyl isobutyrate, methyl valerate, ethyl valerate, propyl valerate, methyl isovalerate, ethyl isovalerate, propyl isovalerate, methyl hexanoate, ethyl hexanoate, propyl hexanoate, methyl heptanoate, ethyl heptanoate, and the like.

The alkyl aryl carbonate, that is used as a raw material for a reaction carried out in the process (3), is not especially limited so long as it is that shown by the aforementioned general formula (VI). However, its practical examples can be cited as follows: methyl phenyl carbonate, ethyl phenyl carbonate, and the like. Any mixture of these compounds may also be used.

The aryl carboxylate, that is used as a raw material for a reaction carried out in the process (4), is not especially limited so long as it is that shown by the aforementioned general formula (VIII). However, its practical examples can be cited as follows: phenyl acetate, methylphenyl acetate (including isomers), ethylphenyl acetate (including isomers), chlorophenyl acetate (including isomers), isopropylphenyl acetate (including isomers), p-methoxyphenyl acetate (including isomers), dimethylphenyl acetate (including isomers), naphthyl acetate (including isomers), phenyl propionate, methylphenyl propionate (including isomers), phenyl butyrate, methylphenyl isobutyrate, methylphenyl valerate (including isomers), phenyl isovalerate, phenyl hexanoate, phenyl heptanoate, and the like.

Examples of the carbonate used as another raw material for a reaction carried out in the process (4) are the aforementioned carbonates that can be used for a reaction carried out in the process (1), and any mixture thereof may also be used.

The molar ratio, in the production process (1), of the aromatic hydroxy compound to the carbonate, that are raw materials, and the molar ratio, in the production process (2), of the aromatic hydroxy compound to the aliphatic carboxylate, that are raw materials, have a lower limit of 1/50, preferably 1/10, more preferably 1/5, and a upper limit of 50, preferably 10, more preferably 5. Since the reactions in the processes (1) and (2) are equilibrium reactions and since their equilibrium is greatly imbalanced to the raw material side rather than to the product side, if one of the raw materials is used in a large excess of the other, the conversion of the raw material used in a smaller amount can be enhanced. However, since the raw material used in a large excess needs to be recycled, it is industrially disadvantageous to enlarge, or otherwise, to reduce the molar ratio.

The molar ratio, in the production process (4), of the carbonate to the aryl carboxylate, that are raw materials, has a lower limit of 1/50, preferably 1/10, more preferably 1/5, and a upper limit of 50, preferably 10, more preferably 5. Since the reaction in the process (4) is an equilibrium reaction having an equilibrium constant of about 0.2 to about 5, if one of the raw materials is used in a large excess of the other, the conversion of the raw material used in a smaller amount can be enhanced. However, since the raw material used in a large excess needs to be recycled, it is industrially disadvantageous to enlarge, or otherwise, to reduce the molar ratio. For example, in the case where the carbonate is a dialkyl carbonate, if it is used in an excessive amount, the conversion of the aryl carboxylate becomes high, but the alkyl aryl carbonate forms as a major product, and the aimed diaryl carbonate does not easily form. Or otherwise, in the case where an excessive amount of aryl carboxylate is used, the conversion of the carbonate becomes high and the diaryl carbonate forms as a major product.

The production process can be carried out using either a batch type reactor or a flow reactor, so reactors used in the present invention are not especially limited. In addition, the process can also be carried out in a reactive-distillation manner. The lower limit of the reaction temperature is 100° C., preferably 140° C., more preferably 160° C. The upper limit of the reaction temperature is 350° C., preferably 300° C., more preferably 280° C. In the case where the reaction temperature is too low, the activity is low, the reaction time or the contact time becomes too long, and the productivity is poor. In addition, too high a reaction temperature is disadvantageous, because a side reaction, such as decarboxylation, tends to occur, or because the inside pressure of the reactor becomes too high.

In the case where the batch type reactor is used, the amount of the catalyst used is not less than 0.1% by weight, preferably not less than 0.5% by weight, and more preferably, not less than 1% by weight, and it is not more than 40% by weight, preferably not more than 30% by weight, and more preferably, not more than 15% by weight. A mixture containing the aimed aryl ester is obtained by filling a predetermined amount of the catalyst of the present invention and the raw materials into the batch type reactor, and then carrying out a transesterification reaction while stirring at a predetermined temperature. The reaction pressure will be a pressure resulting from a vapor pressure of the raw materials. Then, although the reaction time is dependent upon the reaction temperature and the amount of the catalyst, it is generally in a range of 0.1 to 100 hours, preferably in a range of 1 to 30 hours. The catalyst can easily be removed from the resulting reaction liquid containing the catalyst, by centrifugal separation, filtration, or the like.

The aimed aryl ester, a by-product, or an unreacted raw material can be recover from a reaction liquid, from which the catalyst has been removed, generally by distillation, or as occasion demands, by other methods, such as extraction and recrystallization.

In the case where the flow reactor is used, the process can be performed using any reactor of fluidized bed type, fixed bed type, and stirring type. Then, although reaction conditions depend upon the composition of raw materials and the reaction temperature, they are, for example, represented by a liquid hourly space velocity (LHSV) that is defined by dividing a flow rate by volume of flowed raw materials by a volume of a reactor, and the LHSV is not less than 0.05 $hr^{-1}$, preferably not less than 0.01 $hr^{-1}$, and more preferably, not less than 0.02 $hr^{-1}$, and it is not more than 50 $hr^{-1}$ preferably not more than 20 $hr^{-1}$.

Catalyst:

The catalyst of the present invention includes a microporous material containing a metal element belonging to group IV and is insoluble in raw materials, that is, heterogeneous. The microporous material included in the catalyst of the present invention is a solid substance that has very orderly pores in a region of micropore to mesopore, a high crystallinity, and a large specific surface area. Particularly, its pore diameter is in a range of 0.4 to 10 nm, and its crystalline structure is a structure of an MFI type (such as ZSM-5 and TS-1), an MEL type (such as ZSM-11 and TS-2), an AFI type (such as $ALPO_4$-5), a BEA type (such as β-type zeolite), a VFI type (such as VPI-5), an MCM-41 type, or the like. In addition, the microporous material is a substance having a large specific surface area of 100 to 1,500 $m^2/g$.

Examples of the microporous material having micropores are metallosilicates, metalloaluminophosphates, and the like, and they are preferably used, for example, for a reaction wherein the aromatic hydroxy compound is used together as in the process (1) or (2). In addition, examples of the microporous material having mesopores are mesoporous titanosilicates and the like, and they are preferably used, for example, for a reaction from which a product having a large molecular diameter is obtained as in the process (3) or (4).

The metallosilicate is a compound having a crystal lattice in which an aluminum atom of zeolite, that is aluminosilicate, is replaced with another metal element. In the present invention, the metal element includes a metal element belonging to group IV, such as titanium, zirconium, tin and lead. In particular, as the metallosilicate containing titanium as the metal element, there are known titanosilicate having a structure similar to an MFI type structure of ZSM-5 or an MEL type structure ZSM-11; and β-type titanoaluminosilicate, and the like.

The composition of a crystalline metallosilicate containing a metal element belonging to group IV is, for example, represented by an atomic ratio of silicon to one metal element belonging to group IV, and this ratio is not less than 10, preferably not less than 20, and more preferably not less than 25, and it is not more than 500, preferably not more than 200, and more preferably not more than 100. In the case where the atomic ratio of silicon to a metal element belonging to group IV is too small, a ratio of the metal element belonging to group IV is too large, so some of the metal elements belonging to group IV are not incorporated into a crystal lattice, but exist as their oxide outside of the crystal lattice. In the case where the atomic ratio of silicon to a metal element belonging to group IV is too large, the density of the metal element belonging to group IV in a crystal decreases, so the activity decreases.

In addition, the metalloaluminophosphate has a structure in which some of the aluminum or phosphorus atoms of an aluminum phosphate type molecular sieve ($AlPO_4$-n: n is a number denoting a crystal structure) are replaced with other metal elements. The aluminum phosphate type molecular sieve ($AlPO_4$) is a substance having a composition of $AlPO_4$ and a structure in which $AlO_4$ tetrahedrons and $PO_4$ tetrahedrons are alternately and regularly arranged. The aluminophosphate has many sorts of crystal structures, to which n of $AlPO_4$-n is assigned as its identification number. For example, $AlPO_4$-5 is a substance of a 12-oxygen membered ring structure having a pore diameter of about 8 Å, and $AlPO_4$-11 is a substance of a 10-oxygen membered ring structure having a pore diameter of 5 to 6 Å. The metalloaluminophosphate referred to in the present invention, as aforementioned, means a substance having a structure in which some of the aluminum or phosphorus atoms are replaced with metal elements belonging to group IV, such as titanium, zirconium, tin, and lead.

The composition of a crystalline metalloaluminophosphate containing a metal element belonging to group IV is, for example, represented by an atomic ratio of a total of Al and P to one metal element belonging to group IV, and this ratio is not less than 1, preferably not less than 5, and more preferably not less than 10, and it is not more than 500, preferably not more than 100, and more preferably not more than 50. In the case where the atomic ratio is smaller than the above-mentioned lower limit, a ratio of the metal element belonging to group IV is too large, so some of the metal elements belonging to group IV are not incorporated into a crystal lattice, but exist as their oxide outside of the crystal lattice. In the case where the atomic ratio is larger than the above-mentioned upper limit, the density of the metal element belonging to group IV in a crystal decreases, so the activity decreases. In addition, the atomic ratio of P to Al in the crystalline metalloaluminophosphate containing a metal element belonging to group IV is preferably in a range of 0.9 to 1.1. Since some of the 3-valent Al atoms and some of the 5-valent P atoms are replaced with the 4-valent metal elements belonging to group IV, in the case where the atomic ratio of P to Al is outside of the range of 0.9 to 1.1, the entire charge balance may be lost, so an acid site may be formed. As a result, in the case where the aryl carbonate is produced, a side reaction, such as decarboxylation, tends to progress and to form a by-product.

The mesoporous titanosilicate is a compound having a structure in which a silicon atom of mesoporous silicalite is replaced with a titanium atom. Particularly, it is a titanosilicate which has a specific surface area of 500 $m^2/g$ or more, a pore volume of 0.2 $cm^3/g$ or more of pores having a pore diameter of 1.3 to 20 nm, and its atomic ratio of silicon to one titanium atom is in a range of 30 to 1,000. In an aspect of crystal structure, it is a titanosilicate in which at least one peak, in an X-ray powder diffraction pattern after thermal treatment, has an interplanar spacing larger than 1.8 nm. The crystal structure of the mesoporous titanosilicate does not need to be a clear hexagonal crystal system like what is called MCM-41, but may be a cubic crystal system or a lamella structure including layers. The composition of the mesoporous titanosilicate is, for example, represented by an atomic ratio of silicon to one titanium atom, and this ratio is not less than 30, and preferably not less than 60, and it is not more than 100, preferably not more than 500, and more preferably not more than 300. In the case where the atomic ratio of silicon to titanium is too small, a ratio of titanium is too large, so some of the titanium atoms are not incorporated into a crystal lattice, but exist as their oxide outside of the crystal lattice. In the case where the atomic ratio of silicon to titanium is too large, the density of the titanium atom in a crystal decreases, so the activity decreases.

The crystallinity can be judged from X-ray powder diffraction (XRD) analysis. For example, amorphous silicatitania does not show a clear diffraction peak in XRD, but merely shows a broad peak due to amorphous structure. In contrast, as to a crystalline metallosilicate, a crystalline metalloaluminosilicate and the like, there is seen a clear diffraction peak in XRD corresponding to their respective crystalline structure.

The microporous material containing a metal element belonging to group IV, that has the above-mentioned crystalline structure, is effective for the production process of the present invention. Concretely, a crystalline metallosilicate containing a metal element belonging to group IV, a crystalline metalloaluminophosphate containing a metal element belonging to group IV, and the like are particularly effective. Titanium is particularly favorable as the metal element belonging to group IV. A titanosilicate having a structure called TS-1 or TS-2 can preferably be used as the titanosilicate, and TAPO-5 ($AlPO_4$-5 type) can preferably be used as the titanoaluminophosphate.

As to a method for preparing the catalyst of the present invention, there can be employed conventional methods for preparing microporous materials. It is a hydrothermal synthesis method that is particularly preferably used. This method includes the steps of: mixing raw materials for a microporous material, a template, and water; heating them to a predetermined temperature; and thereby crystallizing them.

In the present invention, the transesterification reaction for obtaining an aimed aryl ester and the disproportionation reaction due to the transesterification reaction rapidly progress. In addition, since the catalyst including a microporous material containing a metal element belonging to group IV hardly dissolves into raw materials for reaction (is heterogeneous), the catalyst can easily be separated from a reaction liquid, and there can be prevented the decrease in yield due to a reverse reaction, decomposition, a polymerization reaction and the like because of a residual catalyst in a distillation step as seen in homogeneous reactions. Accordingly, there can efficiently be produced aryl esters that are industrially important.

The aryl esters produced by the production process of the present invention are industrially useful substances as raw materials for resin or as various kinds of intermediate raw materials. In addition, the microporous material containing a metal element belonging to group IV, relating to the present invention, is a useful substance as a heterogeneous catalyst that is used for processes for producing alkyl aryl carbonates, diaryl carbonates, aryl carboxylates, and the like, or for other processes.

BEST MODE FOR CARRYING OUT THE INVENTION

Figure 1:
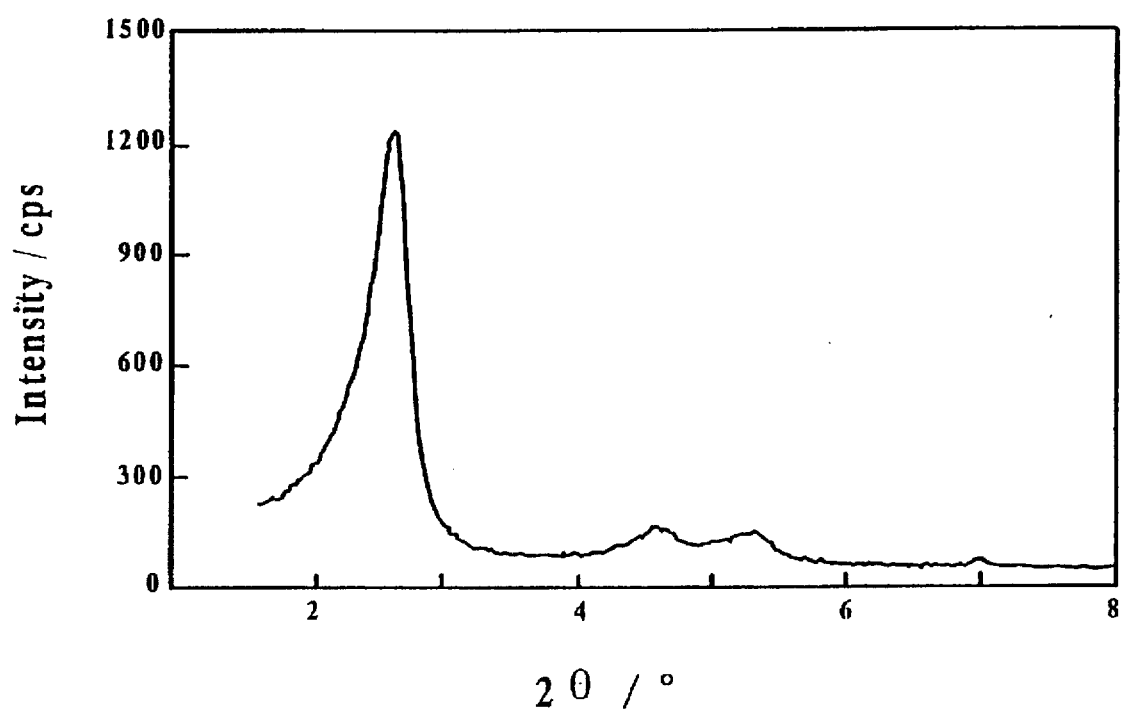
FIG. 1 is a graph showing an X-ray diffraction pattern of the catalyst A-3 that was prepared as is described in Example 3.

Hereinafter, this invention is illustrated by the following examples of some preferred embodiments in comparison with comparative examples not according to the invention. However, this invention is not limited to these examples.

In addition, in the Examples, the conversion and the yield were calculated from the following equations.

a) In the case where the raw material included a carbonate and an aromatic hydroxy compound:

Conversion of carbonate (mol %)=100−(mols of unreacted carbonate that was recovered/mols of supplied raw material carbonate)×100

Yield of aryl carbonate (mol %)=(mols of formed aryl carbonate/mols of supplied raw material carbonate)×100

Yield of by-product (mol %)=(mols of formed by-product/mols of supplied raw material carbonate)×100

(b) In the case where the raw material included an alkyl aryl carbonate:

Conversion of alkyl aryl carbonate (mol %)=100−(mols of unreacted alkyl aryl carbonate that was recovered/mols of supplied raw material alkyl aryl carbonate)×100

Yield of diaryl carbonate (mol %)=(mols of formed diaryl carbonate/mols of supplied raw material alkyl aryl carbonate)×200

The definition of the conversion is the same as in the case (a).

(c) In the case where the raw material included an aliphatic carboxylate and an aromatic hydroxy compound:

Conversion of aliphatic carboxylate (mol %)=100−(mols of unreacted aliphatic carboxylate that was recovered/mols of supplied raw material aliphatic carboxylate)×100

Yield of aryl carboxylate (mol %)=(mols of formed aryl carboxylate/mols of supplied raw material aliphatic carboxylate)×100

(d) In the case where the raw material included aryl carboxylate and a carbonate:

Conversion of aryl carboxylate (mol %)=100 −(mols of unreacted aryl carboxylate that was recovered/mols of supplied raw material aryl carboxylate)×100

Yield of alkyl aryl carbonate (mol %)=(mols of formed alkyl aryl carbonate/mols of supplied raw material aryl carboxylate)×100

Yield of diaryl carbonate (mol %)=(mols of formed diaryl carbonate/mols of supplied raw material aromatic carboxylate)×200

<Preparation of catalyst>

EXAMPLE 1

(preparation of catalyst A-1)

Into a beaker having a capacity of 500 ml was placed 64.5 g of ethyl silicate and then dropwise added 3.2 g of titanium tetrabutoxide at a slow rate, and these materials were stirred at 35° C. for 30 minutes. The resulting mixture was cooled to 0° C., and to this mixture, 266.5 g of a 10% by weight aqueous solution of tetrapropylammonium hydroxide, that had been cooled to 0° C., was slowly dropwise added while maintained at 0° C. After the completion of the dropwise addition, the contents of the beaker were heated to 80°–90° C. and stirred for 5 hours. The resulting mixed solution was poured into an autoclave, and the autoclave was heated to 175° C. and maintained at this temperature for 2 days to carry out hydrothermal synthesis. The resulting gel was filtrated; washed with pure water until the pH of its filtrate was decreased to 8 or less; dried at 120° C. for 8 hours; and then calcined at 540° C. for 3 hours; whereby a crystalline titanosilicate was obtained as catalyst A-1.

As to this catalyst, the atomic ratio of silicon to one titanium atom was 27, and the specific surface area determined by a BET method was 366 m$^2$/g. In addition, the data of X-ray powder diffraction using CuK α rays is shown in Table 1, which shows that the catalyst A-1 has an MFI structure (TS-1 type).

TABLE 1

| 2θ(°) | Intensity I/I$_0$ | 2θ(°) | Intensity I/I$_0$ |
|---|---|---|---|
| 7.94 | 100 | 20.38 | 8 |
| 8.84 | 71 | 23.14 | 95 |
| 9.16 | 14 | 23.76 | 36 |
| 13.22 | 7 | 23.96 | 45 |
| 13.94 | 17 | 24.42 | 28 |
| 14.82 | 25 | 25.92 | 9 |
| 15.56 | 13 | 26.70 | 9 |
| 15.94 | 18 | 26.98 | 10 |
| 17.76 | 9 | 29.32 | 10 |
|  |  | 29.98 | 14 |

EXAMPLE 2

(preparation of catalyst A-2)

Into a beaker having a capacity of 500 ml was placed 34.6 g of phosphoric acid (85% by weight aqueous solution) and then added 73.6 g of tetraethylammonium hydroxide (20% by weight aqueous solution), and these materials were stirred for a while. The resulting mixture was cooled to room temperature, and to this mixture, 18.0 g of ion-exchanged water and 21.9 g of pseudo-boehmite (Cataloid-AP; made by CATALYSTS and CHEMICALS IND. Co., LTD.; containing 70% by weight of Al$_2$O$_3$) were added, and then 15.8 g of titanium tetraisopropoxide was also added. After the contents of the beaker were stirred for 2 hours, the resulting mixed solution was poured into an autoclave to carry out hydrothermal synthesis. The hydrothermal synthesis was carried out by elevating the temperature of the autoclave from room temperature to 160° C. for 90 minutes and then from 160° C. to 200° C. for 3 hours, and then maintaining the autoclave temperature at 200° C. for 4 hours. The resulting solid was filtrated and thrice washed with pure water, and then dried and calcined in the following way: the temperature of the solid was first elevated from room temperature to 120° C. at a rate of 10° C. per minute, maintained at 120° C. for 180 minutes, again elevated to 230° C. at a rate of 10° C. per minute, maintained at 230° C. for 480 minutes, again elevated to 600° C. at a rate of 3° C. per minute, and maintained at 600° C. for 180 minutes; whereby a crystalline titanoaluminophosphate was obtained as catalyst A-2.

As a result of analysis by ICP of this catalyst, the atomic ratio of aluminum to one titanium atom and the atomic ratio of phosphorus to one titanium atom were 6.25 and 6.27 respectively. The specific surface area of the catalyst, determined by a BET method, was 269 m$^2$/g. In addition, the data of X-ray powder diffraction of the catalyst using CuK α rays is shown in Table 2, which shows that the catalyst A-2 has an AlPO$_4$-5 type structure.

TABLE 2

| 2θ(°) | Intensity I/I$_0$ |
|---|---|
| 7.36 | 69 |
| 12.84 | 23 |
| 14.84 | 8 |
| 19.74 | 37 |
| 21.00 | 65 |
| 22.38 | 100 |
| 25.96 | 36 |
| 29.02 | 23 |
| 30.08 | 19 |
| 33.68 | 6 |
| 34.60 | 16 |
| 37.74 | 10 |

EXAMPLE 3

(preparation of catalyst A-3)

Under a nitrogen gas current, 1.3 g of titanium tetrabutoxide was slowly dropwise added to 81.1 g (0.39 mol) of tetraethyl orthosilicate while stirring, and then these materials were heated to about 80° C. and stirred for about 5 hours. The resulting mixture was cooled to room temperature, and to this mixture, there was added a solution that had been prepared by dissolving 0.29 mol of dodecyltrimethylammonium chloride into 231.3 g of 2-propanol, and then the mixture was stirred for minutes. Next, a solution, that had been prepared by dissolving 17.7 g of tetramethylammonium hydroxide (15% aqueous solution) into 35.4 g of 2-propanol, was slowly added over a period of 30 minutes, and the resulting mixture was stirred for about 12 hours. In addition, 42.9 g of tetramethylammonium hydroxide (15% aqueous solution) and 590 g of ion-exchanged water were added, and the temperature was raised to about 90° C. to remove alcohol by distillation for about 5 hours. Then, the residue was poured into a Teflon-made vessel, and the hydrothermal synthesis was carried out at 100° C. for 240 hours. The resulting solid was filtrated, washed, dried, and then thermally treated in air at 540° C. for 6 hours; whereby a mesoporous titanosilicate was obtained as catalyst A-3.

The molar ratio of raw materials used was Si:Ti:dodecyltrimethylammonium chloride: water=1:1/100:0.75:85.5.

Figure 2:
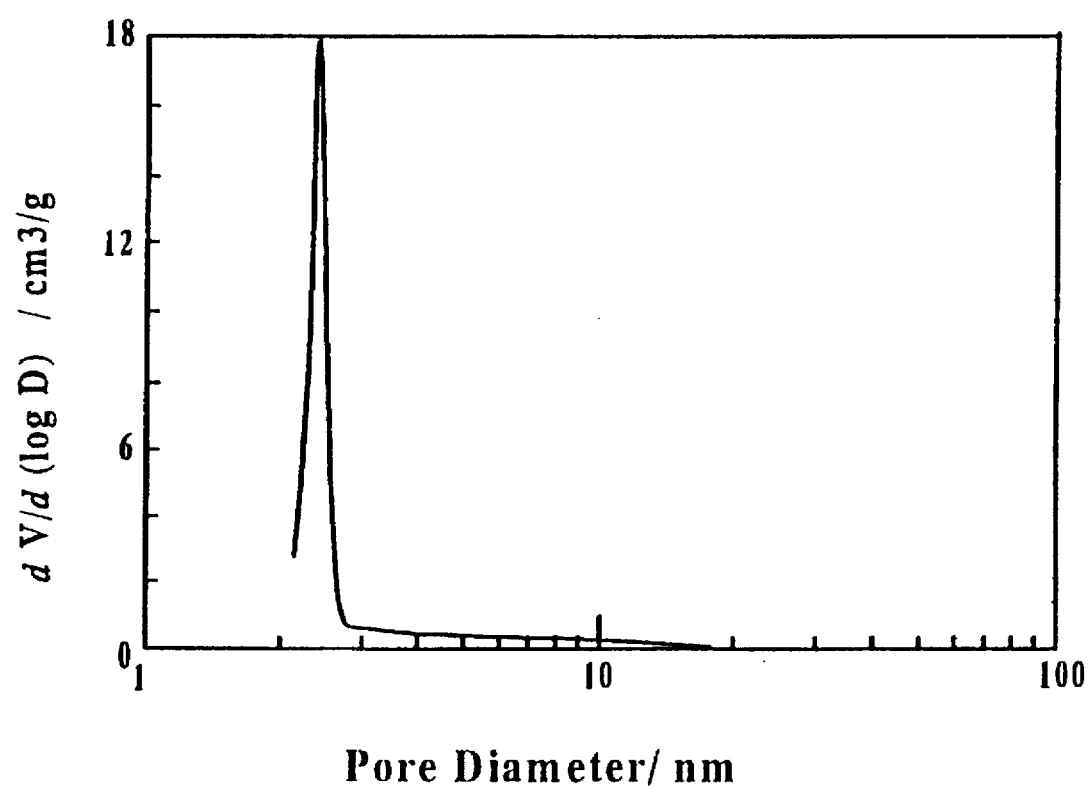
FIG. 2 is a graph showing a pore diameter distribution of the catalyst A-3 that was prepared as is described in Example 3.

An X-ray powder diffraction pattern of the catalyst is shown in FIG. 1. The largest peak of interplanar spacing was a peak of 2.66° in 2θ, and its interplanar spacing was 3.32 nm. In addition, the pore diameter distribution of the catalyst was examined by a nitrogen adsorption method and are shown in FIG. 2. The pore diameter, determined from the pore diameter distribution, was about 2.5 nm. The specific surface area, determined by a BET method, was 1319 m$^2$/g; and the atomic ratio of Si/Ti, determined from ICP emission spectrometry, was 89.9.

EXAMPLE 4

(preparation of catalyst A-4)

A metalloaluminophosphate containing a metal element belonging to group IV, in which the atomic ratio of P to Al was outside of the range of 0.9 to 1.1, was prepared. Its preparation procedure was as follows. Into a beaker having a capacity of 500 ml was placed 34.6 g of phosphoric acid (85% by weight aqueous solution) and then added 73.6 g of tetraethylammonium hydroxide (20% by weight aqueous solution), and these materials were stirred for a while. The resulting mixture was cooled to room temperature, and to this mixture, 18.0 g of ion-exchanged water and 15.6 g of aluminum hydroxide were added, and then 15.8 g of titanium tetraisopropoxide was also added. After the contents of the beaker were stirred for 2 hours, the resulting mixed solution was poured into an autoclave to carry out hydrothermal synthesis. The hydrothermal synthesis was carried out by elevating the temperature of the autoclave from room temperature to 160° C. for 90 minutes and then from 160° C. to 200° C. for 3 hours, and then maintaining the autoclave temperature at 200° C. for 4 hours. The resulting solid was filtrated and thrice washed with pure water, and then dried and calcined in the following way: the temperature of the solid was first elevated from room temperature to 120° C. at a rate of 10° C. per minute, maintained at 120° C. for 180 minutes, again elevated to 230° C. at a rate of 10° C. per minute, maintained at 230° C. for 480 minutes, again elevated to 600° C. at a rate of 3° C. per minute, and maintained at 600° C. for 180 minutes; whereby a crystalline titanoaluminophosphate was obtained as catalyst A-4.

As a result of analysis by ICP of this catalyst, the atomic ratio of aluminum to one titanium atom and the atomic ratio of phosphorus to one titanium atom were 6.15 and 6.95 respectively, which shows that phosphorous is in considerable excess of aluminum. The specific surface area of the catalyst, determined by a BET method, was 247 m$^2$/g. In addition, from the result of X-ray powder diffraction of the catalyst using CuK α rays, it was confirmed that the catalyst A-4 has an AlPO$_4$-5 type structure.

Comparative Example 1 (preparation of comparative catalyst B-1)

A titanium oxide powder having a high surface area (KRONOS (KR-310) made by Titan Kogyo Kabushiki Kaisha) was calcined at 500° C. for 5 hours. The resulting calcined product had a specific surface area of 38 m$^2$/g. This product is hereinafter referred to as catalyst B-1.

Comparative Example 2 (preparation of comparative catalyst B-2)

H-ZSM-5, that is an aluminosilicate having an MFI structure, was prepared. Its preparation procedure was as follows. A silica slurry was prepared by mixing 20 g of a silica powder and 150 g of pure water. To this slurry, there was added a solution that had been prepared by dissolving 3.01 g of sodium aluminate, 4.17 of sodium hydroxide and 0.38 g of tetra-n-propylammonium bromide into 50 g of pure water; whereby hydrothermal synthesis was carried out in an autoclave at 120° C. for 4 hours and then at 180° C. for 12 hours. The resulting product was filtrated and washed, and then ion-exchanged with ammonium ion by two times of treatment with 200 ml of a 1 mol/l aqueous ammonium chloride solution at 60° C. for 24 hours. Then, the product was washed, dried, and then calcined at 500° C. for 2 hours. The resulting calcined product had an Si/Al ratio of 38 and a specific surface area of 431 m$^2$/g by a BET method. This product is hereinafter referred to as catalyst B-2.

Comparative Example 3 (preparation of comparative catalyst B-3)

A silica-titania catalyst having a ratio of Si/Ti=9/1 was prepared. Its preparation procedure was as follows. 7.3 g of titanium tetrachloride was added and dissolved into 50 ml of iced dilute hydrochloric acid, and then 200 ml of water was added. Next, to the resulting mixture, 59 g of silicon tetrachloride was dropwise added. After the completion of the dropwise addition, while the resulting solution was intensively stirred, aqueous ammonia, that had been diluted to twice volume, was added to the solution to adjust the pH of the solution to 7.0. Then, the solution was maintained at 60° C. and further stirred for 2 hours, and then allowed to stand stationary for one night. The resulting precipitate was filtrated, washed, dried at 100° C., and then calcined at 400° C. for 5 hours under a air flow. The resulting calcined product was pulverized and classified into the size of 0.1 to 0.3 mm as catalyst B-3.

<In the case (a)>

EXAMPLE 5

Into an autoclave having a capacity of 200 ml and equipped with a stirrer, pressure gauge, nozzle for sampling, thermometer and external heater for heating were charged 83.9 g of phenol, 16.1 g of dimethyl carbonate and 2.0 g of catalyst A-1 in a dry box, and the inside pressure of the autoclave was increased to 1 MPa using a nitrogen gas. The autoclave was heated to 200° C. to carry out a reaction for 5 hours. The molar ratio of phenol to dimethyl carbonate of raw materials was 5/1, and the amount of the catalyst was 2% by weight. The resulting reaction liquid was analyzed by gas chromatography to determine conversion and yield. Results are shown in Table 3.

The concentration, in the reaction liquid, of Ti that eluted into the reaction liquid was analyzed using an ICP emission spectrometer. The reaction liquid was colorless and transparent, and the concentration of Ti that eluted into the reaction liquid was no more than 0.4 ppm, so there was almost no elution. The present reaction was an equilibrium reaction, and the equilibrium yield is considered to be about a few % in the case where methanol that is a product is not removed. Accordingly, as to the present Example, it can be said that the reaction progressed near equilibrium.

EXAMPLE 6

The reaction of Example 5 was repeated except that catalyst A-2 was substituted for catalyst A-1. Results are shown in Table 3.

The concentration of Ti that eluted into the reaction liquid was no more than 1.7 ppm, and when the reaction was again repeated, the elution of Ti became almost zero.

site was formed. As a result, decarboxylation occurred and anisole was formed due to methylation of phenol.

Comparative Example 4

The reaction of Example 5 was repeated except that 10 g of catalyst B-1 was substituted for catalyst A-1, and that the reaction temperature was changed to 160° C. Results are shown in Table 3.

The reaction liquid was colored into orange, which seems to be due to phenoxide of titanium; the concentration of Ti that eluted into the reaction liquid was 17 ppm, which is 40 times or more of that in the case of catalyst A-1 and shows that a large amount of Ti eluted into the reaction liquid. So the reaction in the present comparative example cannot be said as a heterogeneous reaction and this is a significant problem in practical use.

Comparative Example 5

The reaction of Example 5 was repeated except that 2.0 g of catalyst B-2 was substituted for catalyst A-1. Results are shown in Table 3.

Although catalyst B-2 had the same crystalline structure of an MFI type as that of catalyst A-1, catalyst B-2 did not contain an active component, Ti, and it had too strong action as an acid catalyst. So decarboxylation occurred and only the formation of anisole due to methylation of phenol occurred prior to other reactions.

Comparative Example 6

The reaction of Example 5 was repeated except that 10 g of catalyst B-3 was substituted for catalyst A-1, and that the reaction temperature was changed to 250° C. Results are shown in Table 3.

When the reaction finished, since the catalyst was partially dissolved, it was powdered and formed into a slurry. The reaction liquid was colored into orange, which seems to be due to phenoxide of titanium; the concentration of Ti that eluted into the reaction liquid was 241 ppm, which is 600 times or more of that in the case of catalyst A-1 and shows that a large amount of Ti eluted into the reaction liquid. So it can be said that the reaction substantially occurred in a homogeneous phase.

TABLE 3

|  | Example 5 | Example 6 | Example 7 | Comparative Example 4 | Comparative Example 5 | Comparative Example 6 |
| --- | --- | --- | --- | --- | --- | --- |
| Reaction time (hr) | 5 | 5 | 5 | 5 | 5 | 5 |
| Conversion of DMC (mol %) | 7.7 | 6.2 | 11.9 | 5.9 | 91.1 | 7.2 |
| Yield of MPC (mol %) | 7.5 | 5.6 | 5.5 | 5.9 | 1.8 | 6.1 |
| Yield of DPC (mol %) | 0.1 | 0.1 | 0.1 | 0.0 | 0.0 | 0.1 |
| Yield of anisole (mol %) | 0.1 | 0.5 | 6.2 | 0.0 | 51.6 | 1.0 |

DMC: dimethyl carbonate
MPC: methyl phenyl carbonate
DPC: diphenyl carbonate

EXAMPLE 7

The reaction of Example 5 was repeated except that catalyst A-4 was substituted for catalyst A-1. Results are shown in Table 3.

The concentration of Ti that eluted into the reaction liquid was no more than 1.5 ppm. However, since catalyst A-4 had an atomic ratio of P to Al outside of the range of 0.9 to 1.1, the charge balance of the entire catalyst was lost and an acid <In the case (b)>

EXAMPLE 8

Into an autoclave having a capacity of 100 ml and equipped with a stirrer, pressure gauge, nozzle for sampling, thermometer and external heater for heating were charged 50 g of methyl phenyl carbonate and 1.0 g of catalyst A-3 in a dry box. The inside atmosphere of the autoclave was replaced with a nitrogen gas and then the inside pressure of the autoclave was increased to 200 kPa. The autoclave was heated to 200° C. to carry out a reaction for 5 hours. The amount of the catalyst was 2% by weight. The resulting reaction liquid was analyzed by gas chromatography to determine conversion and yield. Results are shown in Table 4.

The concentration, in the reaction liquid, of Ti that eluted into the reaction liquid was analyzed using an ICP emission spectrometer. The concentration of Ti that was detected in the reaction liquid was no more than 0.5 ppm, so there was almost no elution. The present reaction was an equilibrium reaction, and even when the reaction time was extended, there was seen almost no change in the conversion and the yield. Accordingly, as to the present Example, it can be said that the reaction progressed near equilibrium.

EXAMPLE 9

The reaction of Example 8 was repeated except that catalyst A-2 was substituted for catalyst A-3. Results are shown in Table 4.

Comparative Example 7

The reaction of Example 8 was repeated except that catalyst B-1 was substituted for catalyst A-3. Results are shown in Table 4.

TABLE 4

|  | Example 8 | Example 9 | Comparative Example 7 |
|---|---|---|---|
| Reaction time (hr) | 3 | 5 | 5 |
| Conversion of MPC (mol %) | 32.5 | 32.6 | 22.1 | 7.8 |
| Yield of DPC (mol %) | 32.4 | 32.5 | 21.9 | 7.6 |
| Yield of anisole (mol %) | 0.1 | 0.1 | 0.2 | 0.2 |

MPC: methyl phenyl carbonate
DPC: diphenyl carbonate

<In the case (c)>

EXAMPLE 10

Into an autoclave having a capacity of 200 ml and equipped with a stirrer, pressure gauge, nozzle for sampling, thermometer and external heater for heating were charged 44.8 g of phenol, 55.2 g of methyl valerate and 2.0 g of catalyst A-1 in a dry box, and the inside pressure of the autoclave was increased to 1 MPa using a nitrogen gas. The autoclave was heated to 200° C. to carry out a reaction for 5 hours. The molar ratio of phenol to methyl valerate of raw materials was 1/1, and the amount of the catalyst was 2% by weight. The resulting reaction liquid was analyzed by gas chromatography to determine conversion and yield. Results are shown in Table 5.

The concentration, in the reaction liquid, of Ti that eluted into the reaction liquid was analyzed using an ICP emission spectrometer. The reaction liquid was colorless and transparent, and the concentration of Ti that eluted into the reaction liquid was no more than 0.4 ppm, so there was almost no elution. The present reaction was an equilibrium reaction, and the equilibrium yield is considered to be about a few % in the case where methanol that is a product is not removed. Accordingly, as to the present Example, it can be said that the reaction progressed near equilibrium.

EXAMPLE 11

The reaction of Example 10 was repeated except that 2.0 g of catalyst A-2 was substituted for catalyst A-1, and that 47.9 g of phenol and 52.1 g of methyl butyrate were used as the raw materials. Results are shown in Table 5.

The resulting reaction liquid was colorless and transparent, and the concentration of Ti that eluted into the reaction liquid was no more than 0.3 ppm, so there was almost no elution. The present reaction was an equilibrium reaction, and the equilibrium yield is considered to be about a few % in the case where methanol that is a product is not removed. Accordingly, as to the present Example, it can be said that the reaction progressed near equilibrium.

Comparative Example 8

The reaction of Example 10 was repeated except that 10 g of catalyst B-1 was substituted for catalyst A-1, and that the reaction temperature was changed to 160° C. Results are shown in Table 5.

The reaction liquid was colored into orange, which seems to be due to phenoxide of titanium; the concentration of Ti that eluted into the reaction liquid was 18 ppm, which is 60 times or more of that in the case of catalyst A-1 and shows that a large amount of Ti eluted into the reaction liquid. So the reaction in the present comparative example cannot be said as a heterogeneous reaction and this is a significant problem in practical use.

Comparative Example 9

The reaction of Example 10 was repeated except that 2.0 g of catalyst B-2 was substituted for catalyst A-1. Results are shown in Table 5.

A large amount of by-products were formed other than phenyl valerate. Although the yield of methyl phenyl carbonate seemed to exceed the equilibrium conversion, this is because methanol that was another product was consumed by a side reaction, and the equilibrium was thereby transferred to a side of the formation of phenyl valerate.

TABLE 5

|  | Example 10 | Example 11 | Comparative Example 8 | Comparative Example 9 |
|---|---|---|---|---|
| Reaction time (hr) | 5 | 5 | 5 | 5 |
| Conversion of raw materials (mol %) | 2.7 | 3.7 | 2.6 | 26.3 |
| Yield of product (mol %) | 2.7 | 3.7 | 2.5 | 7.9 |

<In the case (d)>

EXAMPLE 12

Into an autoclave having a capacity of 200 ml and equipped with a stirrer, pressure gauge, nozzle for sampling, thermometer and external heater for heating were charged 33.6 g of dimethyl carbonate, 66.4 g of phenyl valerate and 2.0 g of catalyst A-3 in a dry box, and the inside pressure of the autoclave was increased to 200 kPa using a nitrogen gas. The autoclave was heated to 200° C. to carry out a reaction for 5 hours. The molar ratio of dimethyl carbonate to phenyl valerate of raw materials was 1:1, and the amount of the catalyst was 2% by weight. The resulting reaction liquid was analyzed by gas chromatography to determine conversion and yield. Results are shown in Table 6.

The concentration, in the reaction liquid, of Ti that eluted into the reaction liquid was analyzed using an ICP emission spectrometer. The concentration of Ti that eluted into the reaction liquid was no more than 3 ppm, so there was almost no elution. The present reaction was an equilibrium reaction, and even when the reaction time was extended, there was seen almost no change in the conversion and the yield. Accordingly, as to the present Example, it can be said that the reaction progressed near equilibrium.

EXAMPLE 13

The reaction of Example 12 was repeated except that raw materials including 45.2 g of dimethyl carbonate and 54.8 g of phenyl butyrate was substituted for the raw materials including 33.6 g of dimethyl carbonate and 66.4 g of phenyl valerate. The molar ratio of dimethyl carbonate to phenyl butyrate was 3:2, and the amount of the catalyst was 2% by weight. Results of the reaction are shown in Table 6.

EXAMPLE 14

The reaction of Example 12 was repeated except that raw materials including 67.0 g of diethyl carbonate and 33.0 g of phenyl acetate was substituted for the raw materials including 33.6 g of dimethyl carbonate and 66.4 g of phenyl valerate. The molar ratio of dimethyl carbonate to phenyl acetate was 7:3, and the amount of the catalyst was 2% by weight. Results of the reaction are shown in Table 6.

EXAMPLE 15

The reaction of Example 12 was repeated except that raw materials including 41.7 g of dimethyl carbonate and 58.3 g of phenyl propionate was substituted for the raw materials including 33.6 g of dimethyl carbonate and 66.4 g of phenyl valerate; whereby a reaction liquid containing aryl carbonates was obtained.

This reaction liquid was charged into a four-necked flask, which had a capacity of 200 ml and was equipped with a stirrer and a thermometer and equipped at its upper part with a 10-step distillation column having a condenser and a reflux distributor. The flask was heated to 200° C. to carry out a reaction. As to vapors that were generated, light boiling point components were taken out from the distillation column while the distillation was carried out under conditions where the reflux ratio was 2. After 1 hour from the initiation of the reaction, the inside pressure of the flask was gradually reduced to 100 mmHg, whereby the formed light boiling point components were sufficiently removed by distillation. The reaction was carried out for 5 hours. As a result, 69.0 g of distillate and 31.0 g of distillation residue were obtained. These components were analyzed to determine conversion and yield. Their results are shown in Table 6.

EXAMPLE 16

The reaction of Example 12 was repeated except that catalyst A-2 was substituted for catalyst A-3.

Results are shown in Table 6. Almost no Ti was detected in the resulting reaction liquid. Although the reaction rate was slower than that in use of catalyst A-3, MPC and DPC were formed.

TABLE 6

| | Reaction time (hr) | Conversion of aryl carboxylate (mol %) | Yield alkyl aryl carbonate (mol %) | Yield of diaryl carbonate (mol %) |
|---|---|---|---|---|
| Example 12 | 3 | 62.0 | MPC 43.7 | DPC 18.2 |
| | 5 | 62.2 | MPC 43.8 | DPC 18.3 |
| Example 13 | 5 | 70.8 | MPC 55.0 | DPC 15.7 |
| Example 14 | 5 | 79.0 | EPC 67.4 | DPC 12.4 |
| Example 15 | 5 + 5 | 92.0 | MPC 1.1 | DPC 90.8 |
| Example 16 | 5 | 38.1 | MPC 24.9 | DPC 10.4 |

MPC: methyl phenyl carbonate
EPC: ethyl phenyl carbonate
DPC: diphenyl carbonate

INDUSTRIAL APPLICATION

In the present invention, the transesterification reaction for obtaining an aimed aryl ester and the disproportionation reaction due to the transesterification reaction rapidly progress. In addition, since the catalyst including a microporous material containing a metal element belonging to group IV hardly dissolves into raw materials for reaction (is heterogeneous), the catalyst can easily be separated from a reaction liquid, and there can be prevented the decrease in yield due to a reverse reaction, decomposition, a polymerization reaction and the like because of a residual catalyst in a distillation step as seen in homogeneous reactions. Accordingly, there can efficiently be produced aryl esters that are industrially important.

The aryl esters, relating to the present invention, are industrially useful substances as raw materials for resin or as various kinds of intermediate raw materials. For example, diphenyl carbonate is very useful substance in industry as a raw material for producing a polycarbonate resin with no use of phosgene. In addition, methyl phenyl carbonate and the like can be converted into the above-mentioned diphenyl carbonate by disproportionation due to the transesterification reaction, and are also very useful substances as intermediates. In addition, aryl carboxylates can also be converted into the above-mentioned diphenyl carbonate by transesterification reactions with carbonates, and are also very useful substances as intermediates.

The microporous material containing a metal element belonging to group IV, relating to the present invention, is a useful substance as a heterogeneous catalyst that is used for processes for producing alkyl aryl carbonates, diaryl carbonates, aryl carboxylates, and the like, or for other processes.

We claim:

1. A process for producing an aryl carbonate, which comprises a step of carrying out transesterification between:

a carbonate shown by the following general formula (I):

$$(R^1O)CO(OR^2) \tag{I}$$

where: $R^1$ denotes an alkyl group, a cycloalkyl group, an arylalkyl group, or an aryl group which may have a substituent; and $R^2$ denotes an alkyl group, a cycloalkyl group, or an arylalkyl group; and an aromatic hydroxy compound shown by the following general formula (II):

$$R^3OH \tag{II}$$

where: $R^3$ denotes an aryl group which may have a substituent; in a liquid phase in the presence of a heterogeneous catalyst which comprises a microporous material containing a metal element belonging to group IV;

whereby there is obtained an aryl carbonate shown by the following general formula (III):

$$(R^1O)CO(OR^3) \tag{III}$$

where: $R^1$ denotes an alkyl group, a cycloalkyl group, an arylalkyl group, or an aryl group which may have a substituent; and $R^3$ denotes an aryl group which may have a substituent.

2. A process as in claim 1, wherein said microporous material containing a metal element belonging to group IV is a metallosilicate or a metalloaluminophosphate.

3. A process as in claim 2, wherein said microporous material containing a metal element belonging to group IV is a crystalline titanosilicate or a crystalline titanoaluminophosphate.

4. A process for producing a diaryl carbonate, which comprises a step of carrying out a disproportionation reaction by transesterification of an alkyl aryl carbonate shown by the following general formula (VI):

$$(R^2O)CO(OR^3) \qquad (VI)$$

where: $R^2$ denotes an alkyl group, a cycloalkyl group, or an arylalkyl group; and $R^3$ denotes an aryl group which may have a substituent; in a liquid phase in the presence of a heterogeneous catalyst which comprises a microporous material containing a metal element belonging to group IV;

whereby there is obtained a diaryl carbonate shown by the following general formula (VII):

$$(R^3O)CO(OR^3) \qquad (VII)$$

where: $R^3$ denotes an aryl group which may have a substituent.

5. A process as in claim 4, wherein said microporous material containing a metal element belonging to group IV is a metallosilicate or a metalloaluminophosphate.

6. A process as in claim 5, wherein said microporous material containing a metal element belonging to group IV is a crystalline titanosilicate or a crystalline titanoaluminophosphate.

7. A process for producing an aryl carbonate, which comprises a step of carrying out transesterification between:

an aryl carboxylate shown by the following general formula (VIII):

$$R^5COOR^6 \qquad (VIII)$$

where: $R^5$ denotes an alkyl group, a cycloalkyl group, or an arylalkyl group; and $R^6$ denotes an aryl group which may have a substituent; and a carbonate shown by the following general formula (I):

$$(R^1O)CO(OR^2) \qquad (I)$$

where: $R^1$ denotes an alkyl group, a cycloalkyl group, an arylalkyl group, or an aryl group which may have a substituent; and $R^2$ denotes an alkyl group, a cycloalkyl group, or an arylalkyl group;

in a liquid phase in the presence of a heterogeneous catalyst which comprises a microporous material containing a metal element belonging to group IV;

whereby there is obtained an aryl carbonate shown by the following general formula (IX):

$$(R^7O)CO(OR^8) \qquad (IX)$$

where: $R^7$ denotes an alkyl group, a cycloalkyl group, an arylalkyl group, or an aryl group which may have a substituent; and $R^8$ denotes an aryl group which may have a substituent.

8. A process as in claim 7, wherein said microporous material containing a metal element belonging to group IV is a metallosilicate or a metalloaluminophosphate.

9. A process as in claim 8, wherein said microporous material containing a metal element belonging to group IV is a crystalline titanosilicate or a crystalline titanoaluminophosphate.

* * * * *